(12) United States Patent
Knaan et al.

(10) Patent No.: US 7,771,049 B2
(45) Date of Patent: Aug. 10, 2010

(54) METHOD AND APPARATUS FOR DETECTING SIGHT LINE VECTOR

(75) Inventors: Dotan Knaan, Jerusalem (IL); Adi Shavit, Jerusalem (IL); Dana Shavit, Jerusalem (IL); Kazufumi Suzuki, Tokyo (JP); Norio Ichihashi, Tokyo (JP); Akio Takahashi, Saitama (JP); Akihito Kimata, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 856 days.

(21) Appl. No.: 11/702,910

(22) Filed: Feb. 6, 2007

(65) Prior Publication Data

US 2007/0189742 A1  Aug. 16, 2007

(30) Foreign Application Priority Data

Feb. 7, 2006  (JP)  ............ P. 2006-029428

(51) Int. Cl.
*A61B 3/14* (2006.01)
(52) U.S. Cl. ............ 351/206; 351/209; 351/210
(58) Field of Classification Search .......... 351/206, 351/209, 210, 246, 205; 396/51
See application file for complete search history.

(56) References Cited

U.S. PATENT DOCUMENTS 6,055,322 A * 4/2000 Salganicoff et al. ......... 382/117
6,252,977 B1 * 6/2001 Salganicoff et al. ......... 382/117
2005/0200806 A1    9/2005 Knaan et al.

FOREIGN PATENT DOCUMENTS

JP    2002-017674    1/2002
JP    2003-038442    2/2003

OTHER PUBLICATIONS

Editor—Leslie G. Farkas, Anthropometry of the Head and Face, Second Edition, Raven Press, Ltd., 1185 Ave. of the Americas, New York, New York 10036; 1994 Raven Press, Ltd., pp. 272, 275, 288-289 (Appendix A); pp. 341-343, 349(Appendix B; p. 350 (Appendix C); Cover photograph provided by Superstock, Inc., Birth of Venus, Sandra Boticelli.

* cited by examiner

*Primary Examiner*—Hung X Dang
(74) *Attorney, Agent, or Firm*—Carrier, Blackman & Associates P.C.; William D. Blackman; Joseph P. Carrier

(57) ABSTRACT

A sight line vector detecting method includes: emitting LED light beams from LED light sources arranged on both sides of a camera to an eye; photographing the eye by the camera; acquiring a plane which includes one light source position of the LED light sources, a lens center position of the camera, and a spatial position on a photographed image as to one luminescent spot on a cornea spherical surface, and another plane which includes the other light source position, the lens center position of the camera, and a spatial position on the photographed image as to the other luminescent spot on the cornea spherical surface; acquiring a line of intersection between the two planes; acquiring a center of a cornea ball which is on the intersection line and satisfies a predetermined condition; and acquiring a center of a pupil.

7 Claims, 9 Drawing Sheets

METHOD AND APPARATUS FOR DETECTING SIGHT LINE VECTOR

This application claims foreign priority based on Japanese Patent application No. 2006-029428, filed Feb. 7, 2006, the content of which is incorporated herein by reference in its entirety.

BACKGROUND OF THE INVENTION

1. Field of the Invention

The present invention is related to a method and an apparatus for detecting a sight line vector of a human. Particularly, the present invention is related to a technique for detecting a sight line direction of a person as, for instance, assisting means for an input unit of a computer or when driving a vehicle.

2. Description of the Related Art

When a person wishes to view a scene or an event, the person turns his or her face and eyes to a direction of the scene or the event. That is, the person turns his or her face and eyes to the direction that the person wishes to see in response to an instruction from a brain, images the desired scene or event on retinas, and then, processes images on the retinas so as to acquire necessary information. In this case, turning the eye means making a normal vector of a pupil of the eye correspond to a desired direction, and it is conceivable that a sight line direction (otherwise, sight line vector) is a half straight line (otherwise, vector) which connects a center point of a cornea ball and a center point of the pupil. As a consequence, in order to detect the sight line direction, the sight line direction is obtained by determining a position (coordinates) of the center point of the cornea ball and a position (coordinates) of the center point of the pupil.

Since a pupil is externally exposed, if a distance from a camera up to the pupil can be measured, then center of the pupil can be easily calculated. For instance, by photographing a pupil, a center of the pupil can be acquired from the photographed image. However, it is difficult to directly measure the distance from the camera up to the pupil. Also, since a center of a cornea ball is not externally exposed, it has been so understood that a calculation of this position is complicated. As a consequence, such a sight line vector detecting method and a sight line vector detecting apparatus which are simple and easily understood have not yet been developed.

In order to acquire the center position of the cornea ball, for instance, it is conceivable that a cornea shape measuring apparatuses for measuring a cornea shape, which is used in a hospital's ophthalmology department, may be utilized. However, as can be easily understood from the techniques described in, for example, JP-A-2003-38442 (cornea shape measuring apparatus) and JP-A-2002-17674 (cornea measuring apparatus), these cornea shape measuring apparatuses are not provided to measure entire shape of the cornea ball, but to measure a surface shape on a front side of the cornea. Therefore, it is difficult to measure the center position of the cornea by these cornea shape measuring apparatuses.

As a method of acquiring a sight line direction, for example, there is one method disclosed by HONDA MOTOR CO., LTD. and GENTECH CORPORATION (US publication No. 2005/0200806 A1, "Line-of-sight detection method and apparatus therefor"). FIG. 9 represents a relationship between a structure of an eyeball and a sight line direction. In FIG. 9, a cornea 55 is located on the outer surface of an eyeball 50, and the cornea 55 is regarded as a portion of a spherical surface of a cornea ball 56 shown by a dotted line. A center of the cornea ball 56 is indicated as S, and the cornea ball 56 is a virtual shell having a radius R. An iris 58 for adjusting an incident light amount is positioned on the front side of a lens 57, and a portion which can be seen from an opening of the iris 58 is a pupil 59. A half straight line 60 of an arrow which connects the center S of the cornea ball 56 and a center T of the pupil 59 corresponds to a sight line direction (sight line vector). It should be noted that FIG. 9 indicates a photographed image 61 and a light beam which is emitted from an LED light source B and is reflected at a point "P" on the cornea 55 to reach a center O of a camera lens. The method of acquiring the sight line direction described in US publication No. 2005/0200806 A1 utilizes the below-mentioned four assumptions (1) to (4) which are recognized based on morphologically known data ("Anthropometry of the Head and Face", by L. G. Farkas, Lippincott Williams & Wilkins, 1994). That is, in such a case that, on a face of a subject, a right eye is a point A, a left eye is a point B, and a nose is a point C, the below-mentioned assumptions are made:

distance (A, C)=distance (B, C)
ratio {distance (A, B)/distance (A, C)}=1.0833
distance (A, B)=6.5 cm
diameter of cornea ball=1.54 cm (radius=7.7 mm).

There is a certain question whether all of the above-described assumptions are correctly applied to all of persons. As a consequence, it is necessary to perform a test on the subject. Also, calculation for acquiring the sight line direction is complicated.

SUMMARY OF THE INVENTION

The present invention has been made in view of the above circumstances, and provides a sight line vector detecting method and apparatus, which are capable of acquiring a sight line direction in a simple and clear manner by reducing assumption conditions.

In a first aspect of the invention, a sight line vector detecting method comprises:

emitting LED (light emitting diode) light beams from LED light sources arranged on both sides of a camera to an eye of a subject;

photographing the eye of the subject by the camera;

acquiring a plane which includes one light source position of the LED light sources, a lens center position of the camera, and a spatial position on a photographed image as to one luminescent spot on a cornea spherical surface of the subject;

acquiring another plane which includes the other light source position of the LED light sources, the lens center position of the camera, and a spatial position on the photographed image as to the other luminescent spot on the cornea spherical surface of the subject;

acquiring a line of intersection between said two planes;

acquiring a center position of a cornea ball which is on the intersection line and satisfies a predetermined condition; and acquiring a center of a pupil for acquiring the sight line vector.

Accordingly, an accurate sight line vector can be acquired in a simpler method.

In the sight line vector detecting method, the predetermined condition is that a bisector line of an angle between an incident light from the LED light source and a reflection light of the incident light matches with a normal vector that passes through the luminescent spot on the cornea spherical surface.

In the sight line vector detecting method, the center of the pupil is acquired by acquiring an intersection point of a straight line which passes through the lens center of the camera and a center of the pupil on the photographed image, and a spherical surface having a predetermined radius from the center of the cornea ball.

In a second aspect of the invention, a sight line vector detecting apparatus comprises:

a camera;

LED (light emitting diode) light sources arranged on both sides of the camera;

a controller for controlling the camera to photograph luminescent spots on a cornea ball of an eye when the LED light sources are turned ON simultaneously; and a calculation processing unit for calculating a center point of the cornea ball by using photographed image data of the camera, and calculating a center point of a pupil by using coordinates of the center point of the cornea ball, so as to acquire the sight line vector.

Accordingly, an accurate sight line vector can be quickly acquired by employing the simpler apparatus.

In the sight line vector detecting apparatus, the LED light sources include two sets of the LED light source, and a positional relationship between the two sets of the LED light source and the camera are fixed so as to make up a single unit.

In addition, in accordance with the present invention, there is such an effect that installation of the sight line vector detecting apparatus is easy.

DESCRIPTION OF THE PREFERRED EMBODIMENTS

Referring now to drawings, an embodiment of the present invention will be described.

Figure 1:
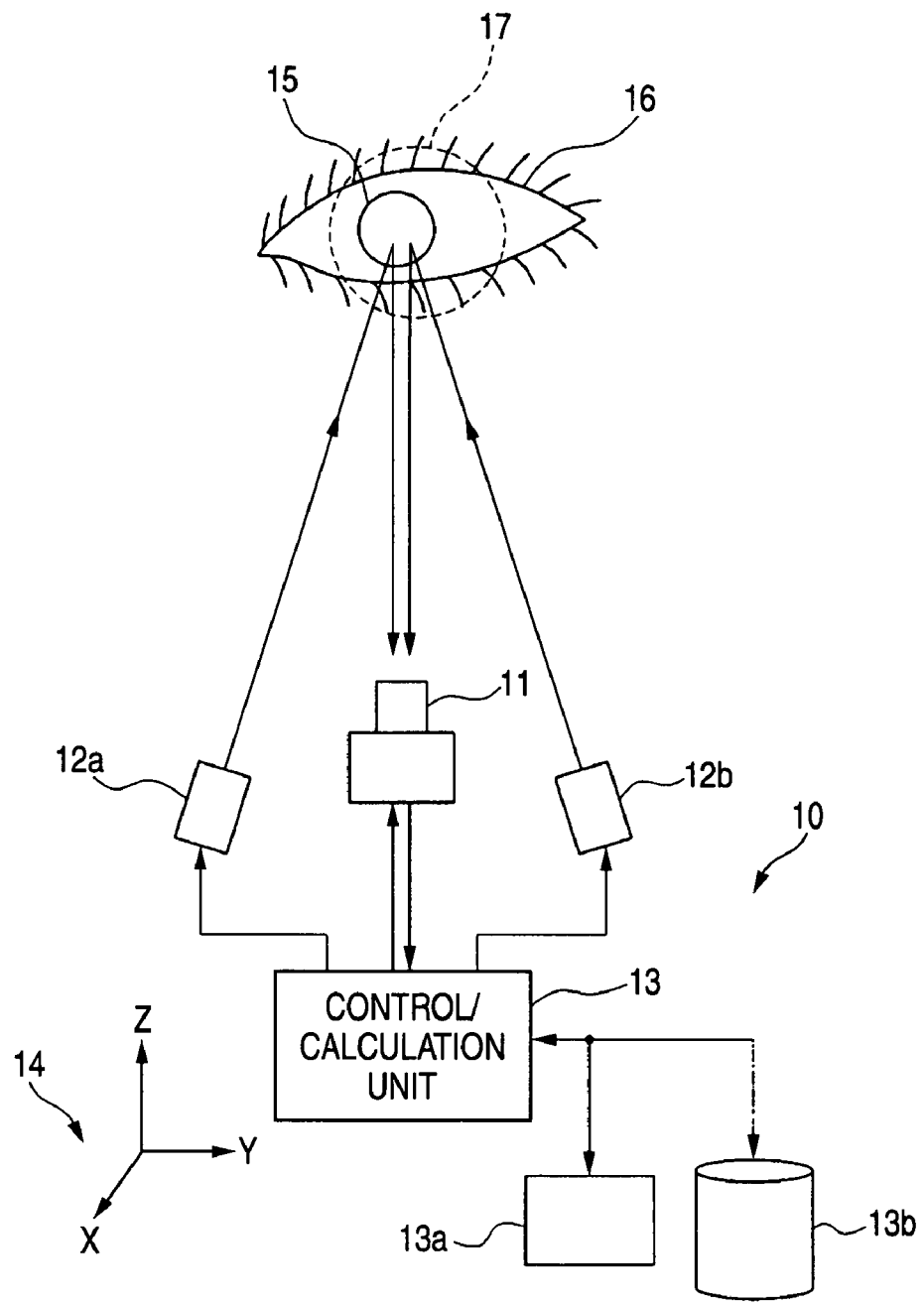
FIG. 1 shows an entire arrangement of a sight line detecting apparatus of an embodiment of the present invention.

FIG. 1 is a diagram showing an overall of an apparatus which detects a sight line direction (sight line vector), according to an embodiment of the present invention. In FIG. 1, a sight line detecting apparatus 10 includes a camera 11, LED (light emitting diode) light sources 12a and 12b, a control/calculation unit 13, an input unit 13a, and a magnetic disk 13b. Reference numeral 16 indicates one eye of a subject, the sight line of which is detected. Also, reference numeral 15 indicates a pupil, and reference numeral 17 indicates a cornea ball. The camera 11 is a digital camera, while a focal distance "f" of a lens 11a of the camera 11 is known. The LED light sources 12a and 12b are point light sources, and are directed to a direction of the eye 16. An eyeball illuminated by the LED light sources 12a and 12b is photographed by the camera 11. It should be noted that positional coordinates of the LED light sources 12a and 12b, and positional coordinates of a lens center of the camera 11 are previously determined in a coordinate system 14. For instance, while the lens center of the camera 11 is defined as an origin, an orthogonal coordinate system (XYZ) 14 is previously determined. The control/calculation unit 13 performs the below-mentioned process operations.

Figure 2:
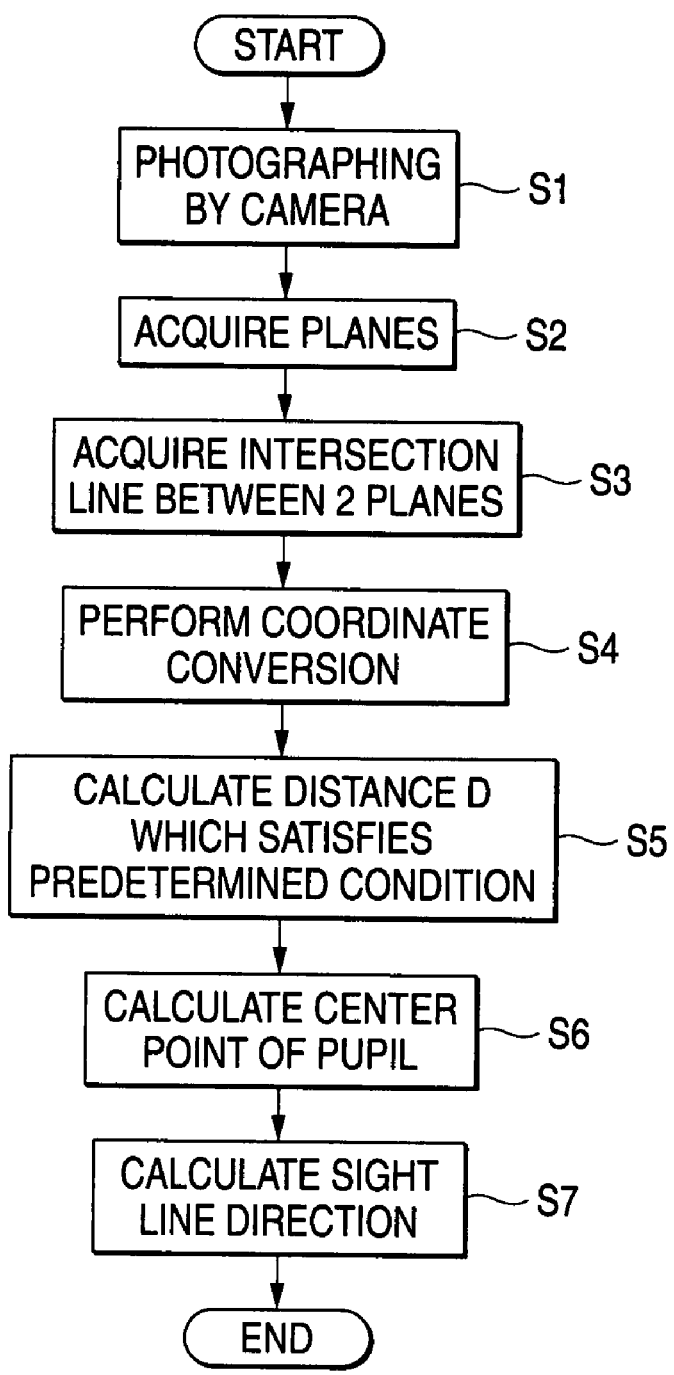
FIG. 2 is a flow chart for describing sequential operations of a sight line detecting method according to an embodiment of the present invention.
Figure 3:
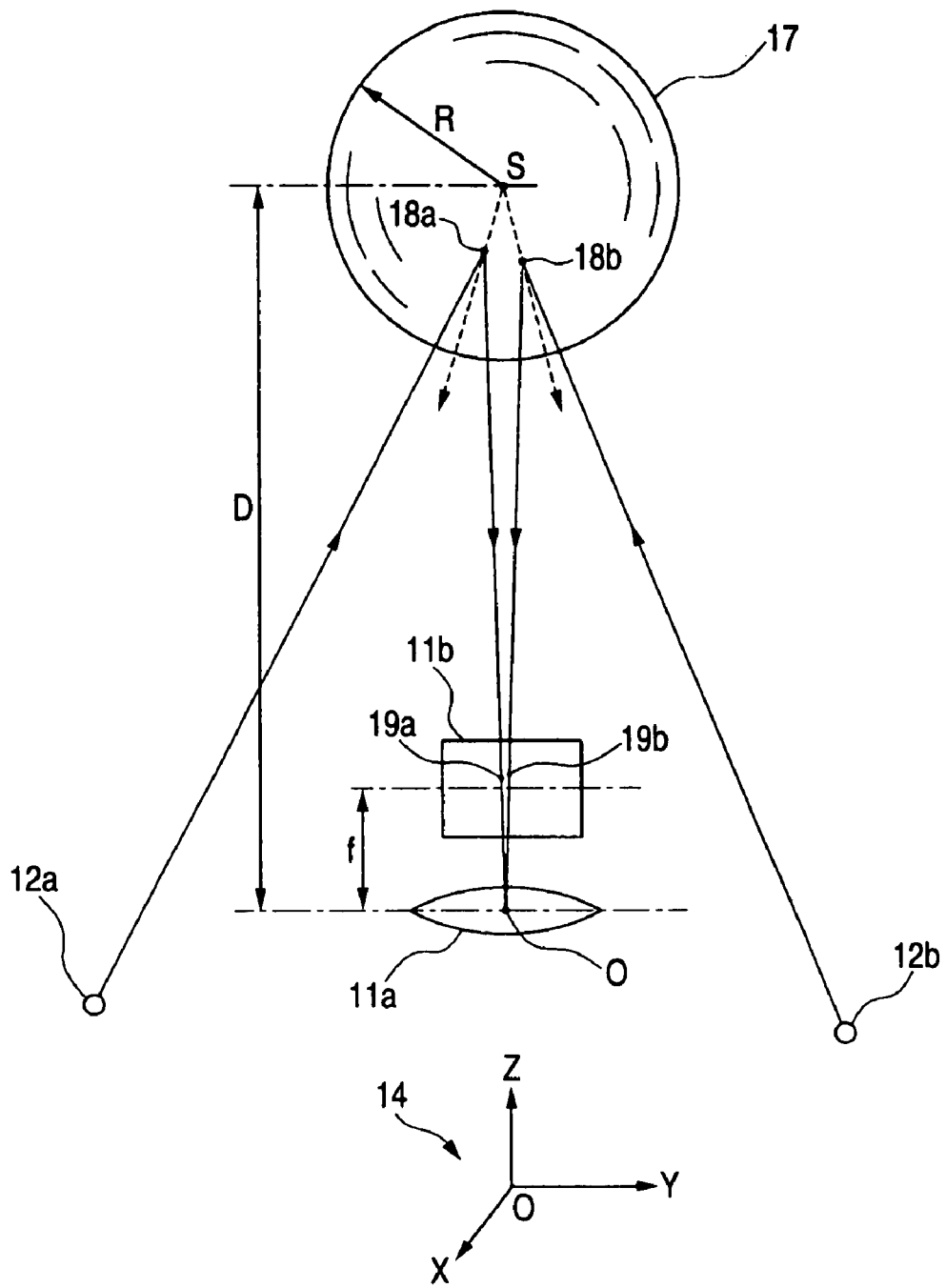
FIG. 3 indicates a relationship between LED light sources and luminescent spots in step S1 of the flow chart.

FIG. 2 is a flow chart for explaining sequential operations of a sight line detecting method of the present embodiment. In FIG. 2, in a step S1, light beams from the LED light sources 12a and 12b are simultaneously emitted toward the cornea ball 17 so as to photograph the cornea ball 17 by the camera 11. This relationship is represented in FIG. 3. The light beams emitted from the LED light sources 12a and 12b are reflected on luminescent spots 18a and 18b on a surface of the cornea ball 17, and the reflected beams pass through a center O of the lens 11a of the camera 11, and then reaches a photographed image plane 11b. Images 19a and 19b of the luminescent spots 18a and 18b are photographed on the photographed image plane 11b. It should also be understood that the photographed image plane 11b is described in front of the lens 11a according to a common practice. In FIG. 3, a distance D indicates such a distance measured from the center O of the lens 11a up to a center point S of the cornea ball 17. In this case, the distance D is unknown, and thus, is calculated in accordance with the below-mentioned sequential operations. For the sake of convenience, the origin of the XYZ coordinate system 15 is defined at the center O of the lens 11a, the Z axis is determined to direct toward the cornea ball 17; and both the X axis and the Y axis are appropriately determined. As a consequence, coordinates of the LED light sources 12a and 12b in the XYZ coordinate system are previously determined.

Figure 4:
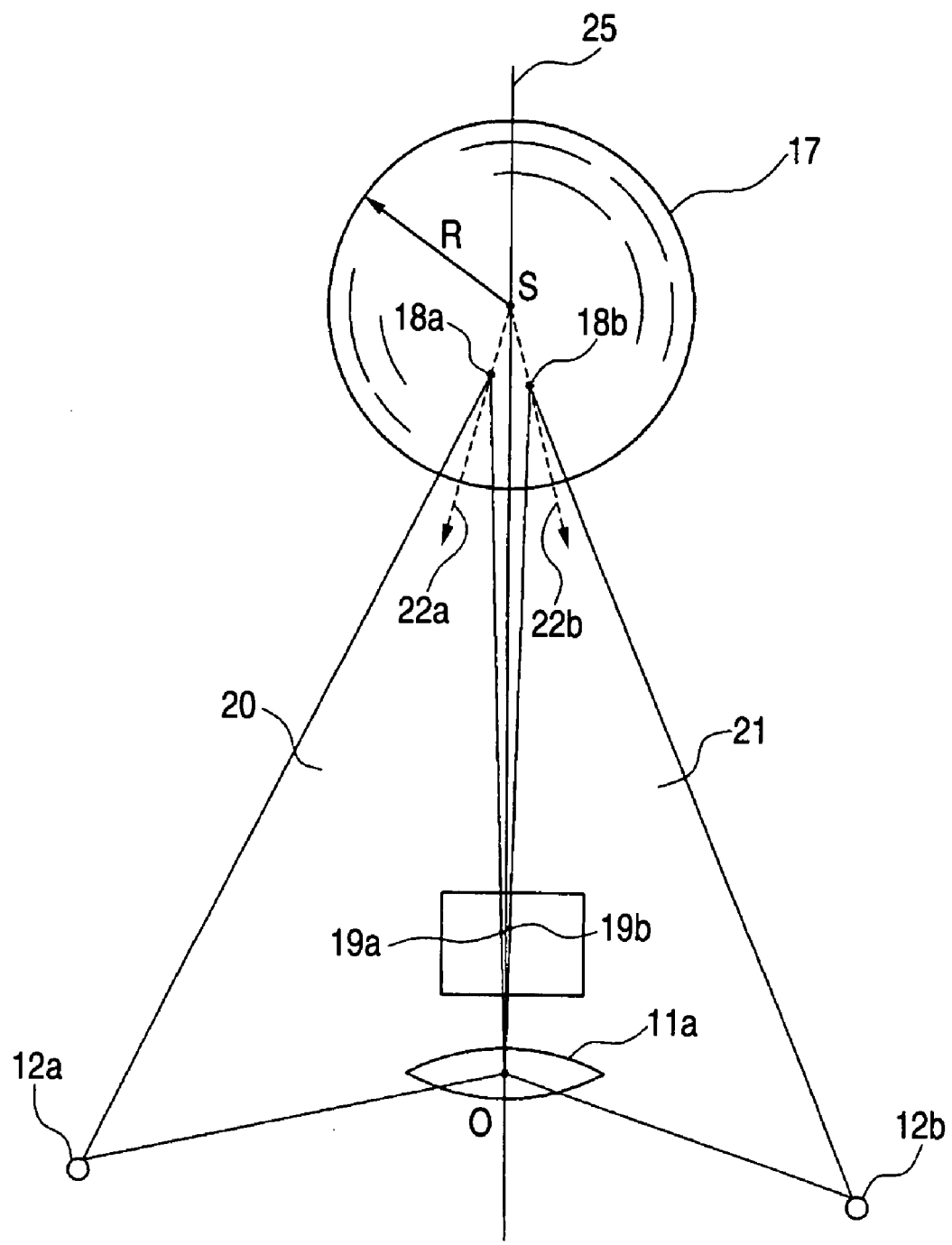
FIG. 4 shows an intersection line between 2 planes in step S3.

In a step S2, firstly, positions (coordinates) of the images 19a and 19b of the luminescent spots 18a and 18b in the plane coordinate system are read out from the photographed image on the photographed image plane 11b, and coordinates of the luminescent spots 19a and 19b on the three-dimensional coordinate system (XYZ coordinate system) are obtained by utilizing a focal distance "f" (alternatively, it is also possible to set f=1). Next, a plane 20 is obtained which passes through 3 points, namely, the center O of the lens 11a, the LED light source 12a, and the image 19a of the luminescent spot 18a. Also, another plane 21 is obtained which passes through 3 points, namely, the center O of the lens 11a, the LED light source 12b, and the image 19b of the luminescent spot 18b (refer to FIG. 4). As indicated in FIG. 4, the plane 20 contains the luminescent spot 18a, and a normal vector 22a at the luminescent spot 18a. Similarly, the plane 21 contains the luminescent spot 18b, and a normal vector 22b at the luminescent spot 18b. Accordingly, both of the planes 20 and 21 contain a center S of the cornea ball 17.

Figure 5:
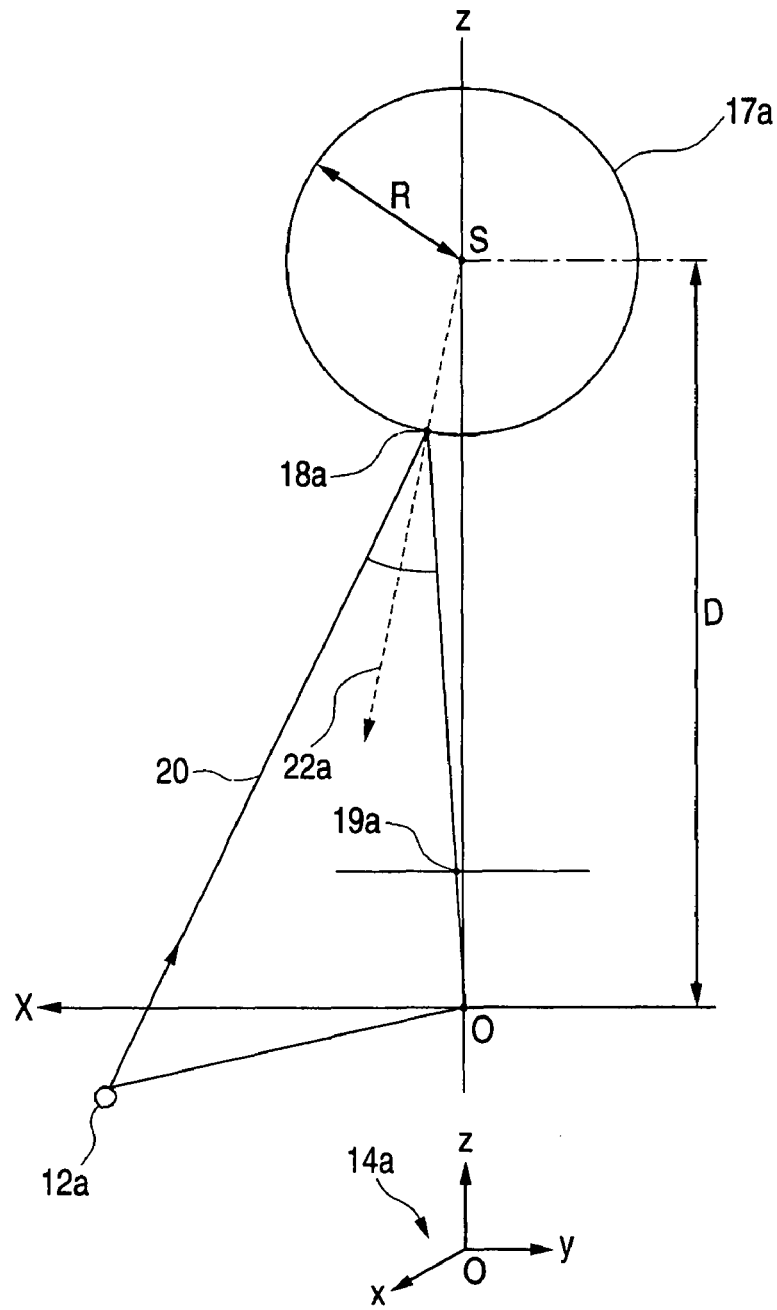
FIG. 5 is a diagram in which coordinate axes are converted in such a manner that the luminescent spots exist on a plane of this sheet of FIG. 5, in step S4.

In a step S3, simultaneous equation of two planes, the plane 20 and the plane 21, are calculated so as to obtain an intersection line 25. A center S of the cornea ball 17 is present on the intersection line (straight line) 25. In a step S4, the XYZ coordinate system is converted into an xyz coordinate system so that the plane 20 corresponds to the sheet of FIG. 5. In other words, as shown in FIG. 5, the XYZ coordinate system is rotated so that the origin O stays in its original position, the z axis passes through the center S of the cornea ball 17, and the LED light source 12a is contained in the xz plane. As a result, a cross section which passes through the center S of the cornea ball 17 appears as a circle 17a on the sheet of FIG. 5. Also, the luminescent point 18a and the image 19a appear on the sheet of FIG. 5. Further, the path of the light beam emitted from the LED light source 12a, and the normal vector 22a which passes through the luminescent point 18a appear on the sheet of FIG. 5.

Figure 6:
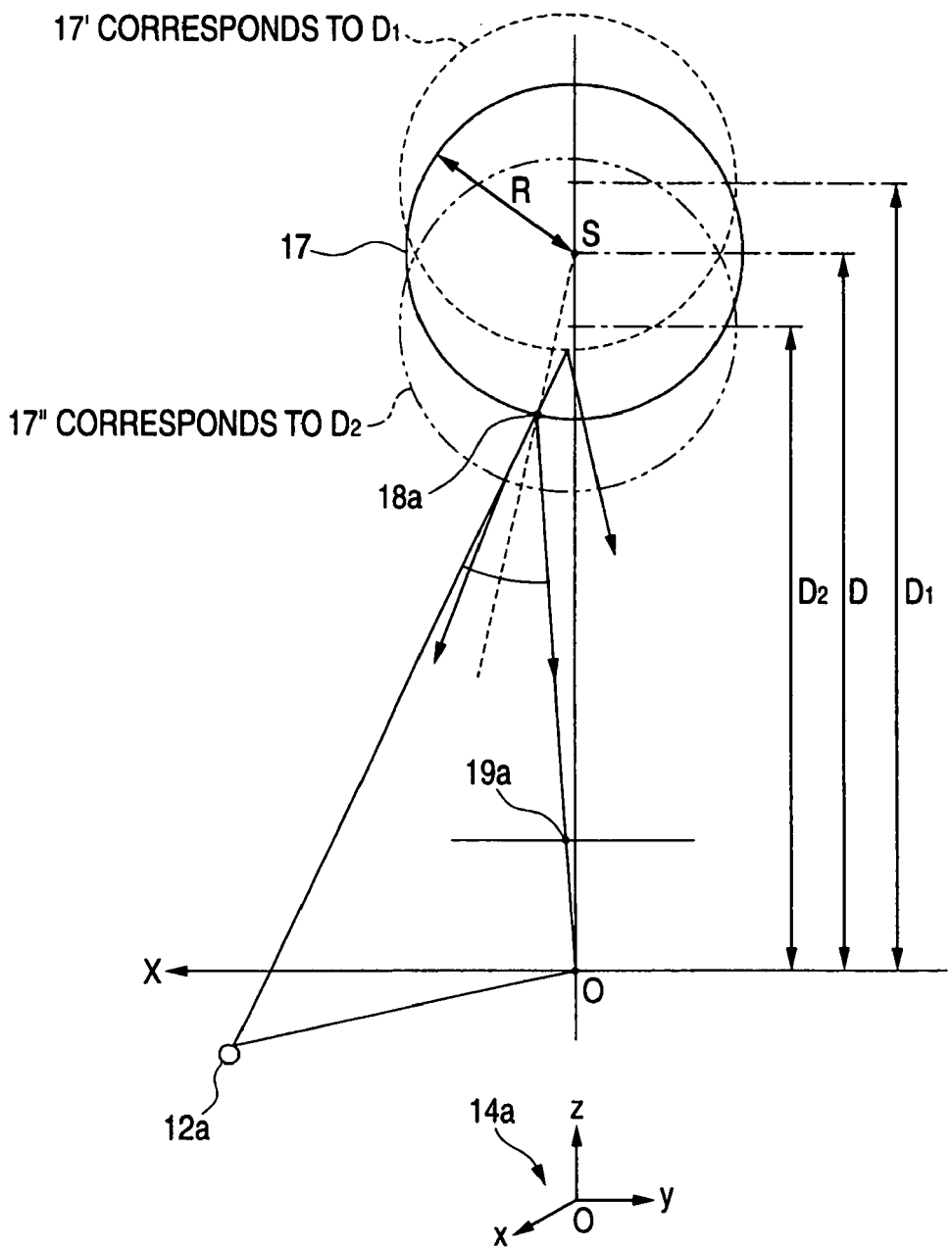
FIG. 6 represents a change in a distance "D" and a change in a direction of reflection light in step S5.

In a step S5, a distance D (distance between the origin O and the center S of the cornea ball 17) which satisfies the below-mentioned conditions is obtained. It is assumed that a diameter (otherwise, radius) of the cornea ball 17 is already known (namely, diameter=14.8 mm, or radius=7.4 mm). This assumption is recognized as morphologically known data. By using the assumption, the distance D is determined so that an incident angle and a reflection angle at the luminescent point of the cornea ball 17 (cross section 17a) are identical, and furthermore, reflection light passes through the origin O (or image 19a). As to the plane 21, the sequential operations of the step S4 and the step S5 are carried out in a similar manner so as to calculate a distance Da. The distance D should originally match with the distance Da. In such a case that these distances D and Da do not match due to a measurement error or the like, an average value of these distances D and Da may be employed as the actual distance D. FIG. 6 is a diagram in which a path of a reflection light beam when a distance (D) between the origin O and the center S of the cornea ball 17 is correct is compared with another path of a reflection light beam when distances (D1 and D2) between the origin O and the center S of the cornea ball 17 are in error. As can be understood from this drawing, the distance D can be obtained by a repetition calculation.

In a step S6, a center 28 of the pupil 15 is calculated. Firstly, coordinates of the center 26 of the pupil are obtained in the original coordinate system 14 from the photographed image plane 11b. Next, a conversion of the coordinate axes (namely, rotation of coordinate axes) is carried out so that the Z axis passes through the center S of the cornea ball 17. In this case, the X axis (or Y axis) may be arbitrarily determined. The new orthogonal coordinate system whose coordinate axes are converted is defined as a coordinate system (X', Y', Z') 14b. Then, the coordinates of the pupil center 26 in the coordinate system 14 are converted into the new orthogonal coordinate system 14b so as to obtain the converted coordinates.

Figure 7:
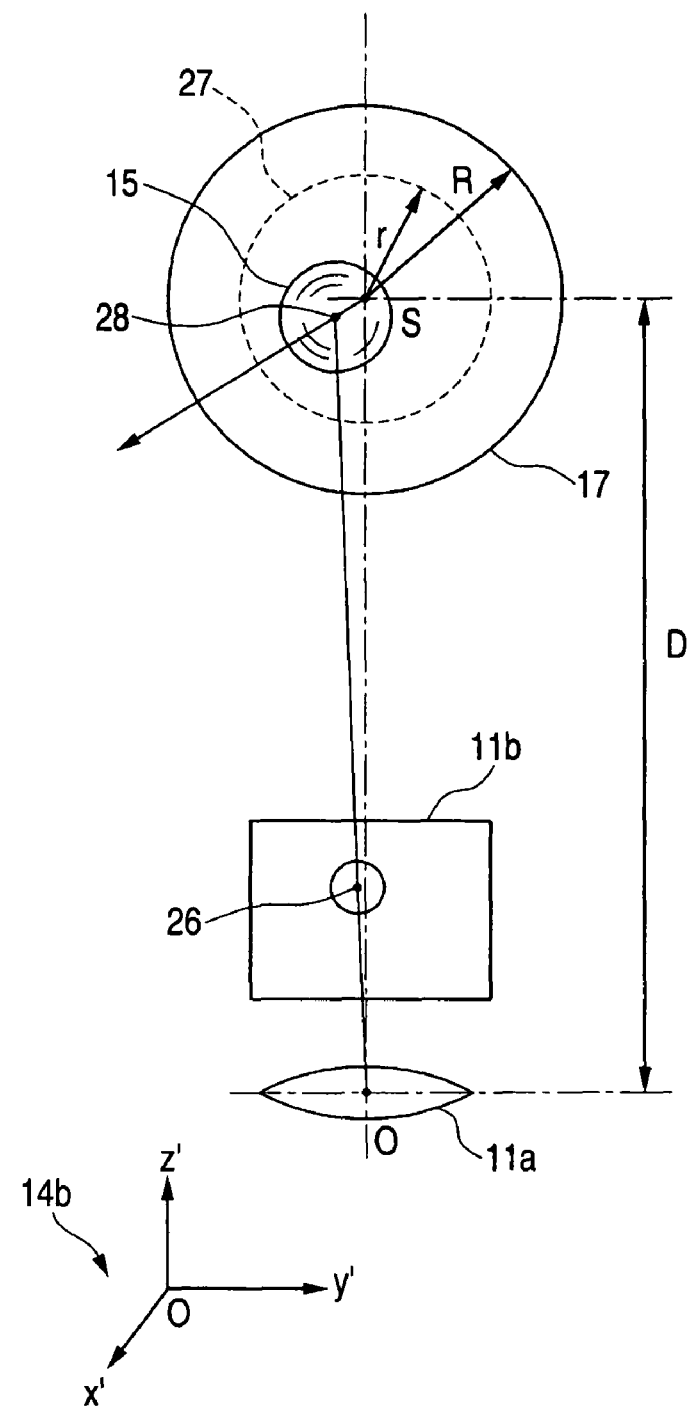
FIG. 7 is an explanatory diagram for obtaining a center of a pupil in step S6.

In this case, a spherical surface 27 of the pupil 15 is regarded as a portion of a spherical surface having a radius "r" (r=4.5 mm) and the center S of the cornea ball 17 as a center. This assumption is recognized based on the morphologically known data. FIG. 7 is an explanatory diagram for acquiring a center point 28 of the pupil 15. A half straight line is drawn from a center point of the camera lens 11a to pass through the center 26 of the pupil on the coordinate system 14b so as to acquire the intersection point 28 between this half straight line and the spherical surface 27. This intersection point 28 is obtained by solving the simultaneous equation of the equation of the spherical surface 27 and the half straight line. This intersection point 28 corresponds to the center point 28 of the pupil 15.

In a step S7, a sight line direction is acquired. As a consequence, the sight line direction is a vector which passes through the center point 28 of the pupil 15 from the center point S of the cornea ball 17.

Figure 8A:
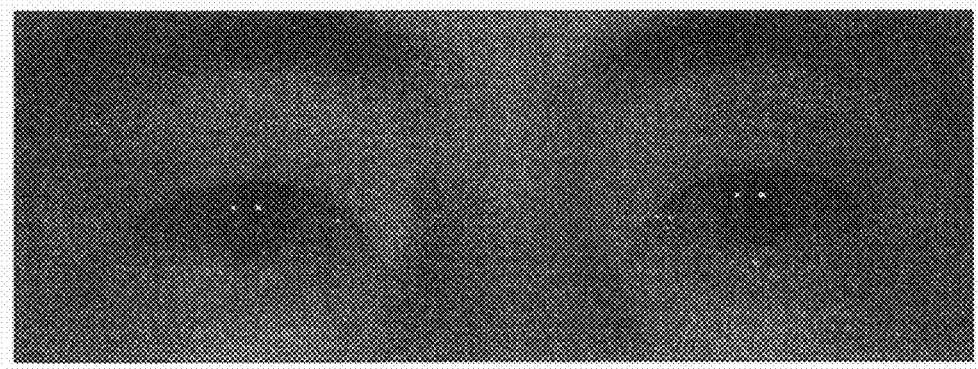
FIGS. 8A and 8B represent examples of photographed images.
Figure 8B:
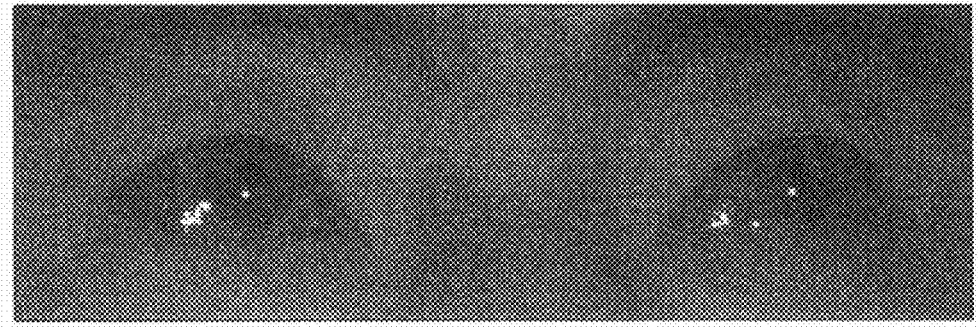
Figure 9:
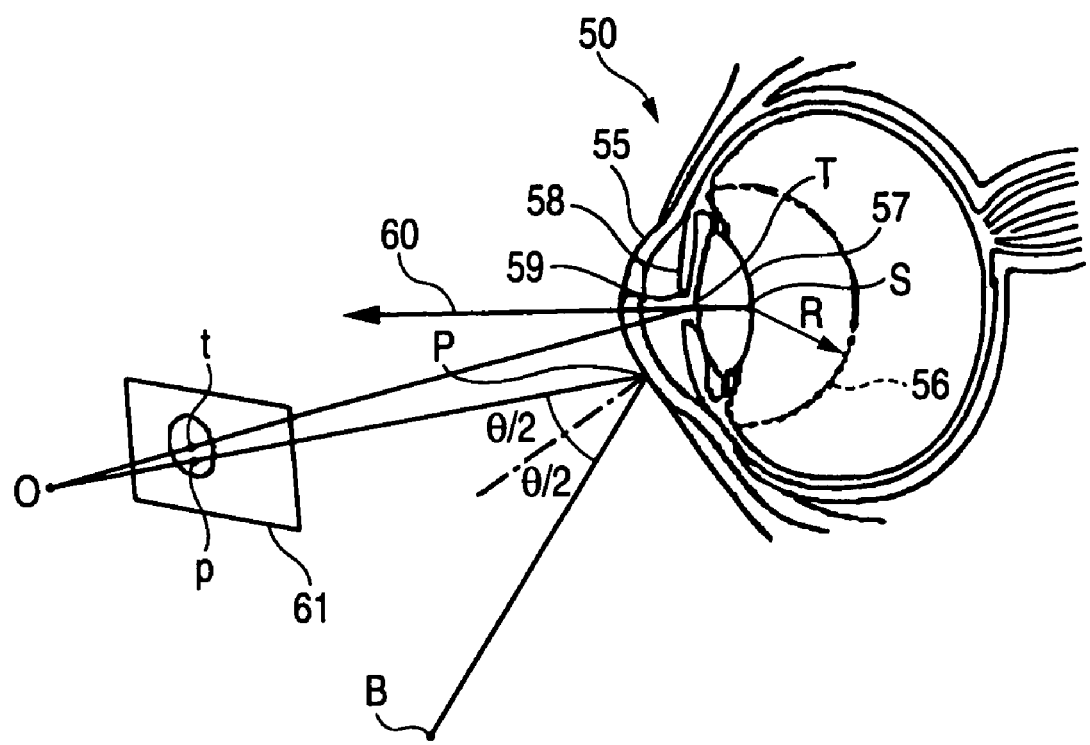
FIG. 9 indicates a structure of an eye and a sight line vector.

FIG. 8A and FIG. 8B are diagrams representing examples of photographed images. FIG. 8A is a photographed image in a state that the subject views a substantially horizontal direction, and FIG. 8B is a photographed image in a state that the subject views an upper direction. If a sight line direction (sight line vector) is acquired from a right eye and a left eye of the subject shown in FIG. 8, then a direction to which the subject pays his or her attention can be detected. As can be understood from the above-descried explanations, the sight line vector detecting method of this embodiment merely utilizes an assumption about a size (radius=7.4 mm) of the cornea ball and an assumption that the spherical surface of the pupil is a part of the spherical surface having the radius of 4.5 mm. As a consequence, there is a small margin as to an occurrence of errors, so that an accurate sight line vector can be obtained. Also, the calculations utilized in this sight line vector detecting method are merely performed by rotating the coordinate systems and solving the simultaneous equations, and therefore, can be easily and quickly carried out.

Although the embodiment of the present invention has been described in detail based upon the drawings, the technical scope of the present invention is not limited thereto. For example, coordinate axes in the coordinate conversions may be suitably determined. Also, as to a method of the repetition calculation for obtaining the distance D, the above-described calculation method may be alternatively changed.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A sight line vector detecting method, comprising:
   emitting LED (light emitting diode) light beams from LED light sources arranged on both sides of a camera to an eye of a subject;
   photographing the eye of the subject by the camera;
   acquiring a plane which includes one light source position of the LED light sources, a lens center position of the camera, and a spatial position on a photographed image as to one luminescent spot on a cornea spherical surface of the subject;
   acquiring another plane which includes the other light source position of the LED light sources, the lens center position of the camera, and a spatial position on the photographed image as to the other luminescent spot on the cornea spherical surface of the subject;
   acquiring a line of intersection between said two planes;
   acquiring a center position of a cornea ball which is on the intersection line and satisfies a predetermined condition; and
   acquiring a center of a pupil for acquiring the sight line vector.

2. The sight line vector detecting method as claimed in claim 1, wherein the predetermined condition is that a bisector line of an angle between an incident light from the LED light source and a reflection light of the incident light matches with a normal vector that passes through the luminescent spot on the cornea spherical surface.

3. The sight line vector detecting method as claimed in claim 2, wherein the center of the pupil is acquired by acquiring an intersection point of a straight line which passes through the lens center of the camera and a center of the pupil on the photographed image, and a spherical surface having a predetermined radius from the center of the cornea ball.

4. The sight line vector detecting method as claimed in claim 1, wherein the center of the pupil is acquired by acquiring an intersection point of a straight line which passes through the lens center of the camera and a center of the pupil on the photographed image, and a spherical surface having a predetermined radius from the center of the cornea ball.

5. The sight line vector detecting method as claimed in claim 1, wherein the sight line vector is a vector passing from the center of the cornea ball to the center of the pupil.

6. A sight line vector detecting apparatus, comprising:
a camera;
LED (light emitting diode) light sources arranged on both sides of the camera;
a controller for controlling the camera to photograph luminescent spots on a cornea ball of an eye when the LED light sources are turned ON simultaneously; and
a calculation processing unit for calculating a center point of the cornea ball by using photographed image data of the camera, and calculating a center point of a pupil by using coordinates of the center point of the cornea ball, so as to acquire the sight line vector.

7. The sight line vector detecting apparatus as claimed in claim 6, wherein the LED light sources include two sets of the LED light source, and
a positional relationship between the two sets of the LED light source and the camera are fixed so as to make up a single unit.

\* \* \* \* \*